(12) United States Patent
Büchler

(10) Patent No.: US 8,278,949 B2
(45) Date of Patent: Oct. 2, 2012

(54) METHOD AND SENSOR FOR DETERMINING THE PASSIVATING PROPERTIES OF A MIXTURE CONTAINING AT LEAST TWO COMPONENTS, WHICH ARE CEMENT AND WATER

(75) Inventor: Markus Büchler, Bülach (CH)

(73) Assignee: VSL International AG, Bern (CH)

( * ) Notice: Subject to any disclaimer, the term of this patent is extended or adjusted under 35 U.S.C. 154(b) by 660 days.

(21) Appl. No.: 12/440,783

(22) PCT Filed: Sep. 11, 2006

(86) PCT No.: PCT/EP2006/066241
§ 371 (c)(1),
(2), (4) Date: Jul. 15, 2009

(87) PCT Pub. No.: WO2008/031453
PCT Pub. Date: Mar. 20, 2008

(65) Prior Publication Data
US 2010/0039125 A1     Feb. 18, 2010

(51) Int. Cl.
*G01R 27/08* (2006.01)
(52) U.S. Cl. ..................................................... 324/693
(58) Field of Classification Search .................. None
See application file for complete search history.

(56) References Cited

U.S. PATENT DOCUMENTS

| | | |
|---|---|---|
| 3,788,962 A | 1/1974 | Frenck |
| 4,575,678 A * | 3/1986 | Hladky ........................ 205/776 |
| 5,015,335 A | 5/1991 | Green |
| 5,239,268 A | 8/1993 | Moriguchi |

FOREIGN PATENT DOCUMENTS

| | | |
|---|---|---|
| DE | 2335419 A1 | 2/1975 |
| EP | 0867695 A2 | 9/1998 |
| JP | 01254855 A * | 10/1989 |
| SU | 1727942 A2 | 4/1992 |
| WO | 96/30741 A | 10/1996 |
| WO | 2004/010104 A2 | 1/2004 |

OTHER PUBLICATIONS

Pruckner, F. et al: "In-situ monitoring of the efficiency of the cathodic protection of reinforced concrete by electrochemical impedance spectroscopy" Electrochimica ACTA, Elsevier Science Publishers, Barking,k GB, vol. 41, No. 7, May 6, 1996, pp. 1233-1238, XP004019457, ISSN: 0013-4686. The whole document.

International Search Report, PCT/EP2006/066241 dated Feb. 5, 2007.

* cited by examiner

*Primary Examiner* — Paresh Patel
(74) *Attorney, Agent, or Firm* — Pearne & Gordon LLP

(57) ABSTRACT

A method for determining the passivating properties of a mixture containing cement and water. Taking three elements that are referred to as first-third electrodes. Fixing at least one electrode on a support such that the electrodes are electrically insulated reciprocally and the mixture is able to come in contact with a face on each electrode. Applying between the first and third electrodes a direct current, referred to as first direct current, of predetermined intensity value and predetermined polarity, resulting in electrolytic reactions on the third electrode for a first duration, and then measuring voltage between the second and third electrodes. Storing the measurement for the variation of said voltage, comparing the variations in the voltage with predetermined data defining at least whether or not a mixture has passivating properties, and determining at least whether or not the mixture has such passivating properties.

16 Claims, 8 Drawing Sheets

METHOD AND SENSOR FOR DETERMINING THE PASSIVATING PROPERTIES OF A MIXTURE CONTAINING AT LEAST TWO COMPONENTS, WHICH ARE CEMENT AND WATER

The present invention relates to a method for determining the passivating properties of a mixture containing at least two components, which are cement and water. The invention also relates to a method which indirectly allows checking the filling of a vessel, such as an encasing tube, with the aforementioned mixture. The invention relates furthermore to a sensor for implementing said method.

TECHNICAL FIELD

Tendons used for the construction of suspended and stayed structures, such as suspension bridges, cable-stayed bridges, stadium roofs, buildings, telecommunications towers, post-tensioned bridges, containment structures, etc. comprise a plurality of strands, wires or bars (hereinafter only strands are referred to, but in a non-limiting way) embedded in a medium made up of material capable of hardening, such as a mixture of cement and water (grout) hereinafter referred to as "mixture". A tendon is connected to structures by means of anchoring devices. A tendon also comprises a tube, said encasing tube, in which the strands of the tendons are introduced before the mixture is poured in this encasing tube in such a manner as to completely fill said encasing tube. The filling with mixture ensures that the strands of the tendon are in contact along their entire length with the alkaline pore solution of the mixture. Passivation of the strands is thereby achieved, and thus a far-reaching/long-term corrosion protection of the steel.

Problems arise with incomplete filling with mixture, however. Zones without protective passivation thereby result on the steel strands, which, with formation of condensation water and reaction with $CO_2$ from the air, can result in an onset of corrosion, quick loss of sectional area and, in the extreme case, failure of the tendon. Additionally the contamination of the mixture with chloride, or chloride reaching the tendon from the surface of the structure, can compromise the passivating properties of the mixture, and thus lead to corrosion. In certain cases, even collapse of structures has resulted.

BACKGROUND ART

Since injection is of such great importance, great efforts are being made in developing this process, the materials used and the sequence of operations. If done correctly, complete filling of the encasing tube with mixture can be ensured. There nevertheless remains a certain amount of uncertainty about whether errors may have occurred during mixing and injection of the mixture. Extensive measures are often taken to eliminate this uncertainty and exclude faulty manipulations. For example, a hole is drilled in the region of the anchorage, and the filling is assessed visually. An alternative is the use of transparent covers which permit visual checking of the tendon filling during and after the setting process at accessible locations. In addition, in individual cases, the filling of the tendon is checked at points using radar.

Most of these measurements cannot be carried out until after successful injection, however, and require considerable time, effort and investment in measuring. Some locations are not accessible for these methods. During the injection procedure, however, the time up to completion of the operation is severely limited by the incipient setting of the mixture.

It is therefore important to have information during the injection operation about a possibly insufficient filling with mixture at all critical 20 locations. Only in this way can a higher degree of filling be achieved through additional measures.

It has been proposed that this control is possible by means of a filling sensor that detects the wetting of the sensor by mixture, as described in JP2000230915.

Filling the tendon with mixture does not suffice in every case to ensure corrosion protection, however. Thus corrosion damage can occur even though the tendon has been completely filled with mixture. This is possible, for example, if a blast furnace cement with minimal alkalinity or mixing water polluted with chloride is used. Under certain circumstances, such situations cannot be excluded even with optimal quality control. Chlorides can also penetrate subsequently into the encasing tube through leaky places in the concrete, and, at high enough concentrations, can trigger corrosion.

DISCLOSURE OF INVENTION

One of the objects of the invention is therefore to provide a method and means of detecting the complete filling of the tendon with mixture, thus ensuring corrosion protection of steel strands.

This object is achieved according to the invention through the features mentioned in claim 1.

The main object of the invention is that the filling of the tendon be detected in critical zones by determining the possible wetting of an electrode with a mixture having passivating properties. Too low a pH value (pH relating to alkalinity), too high a chloride content, the presence of other aggressive substances or the presence of bleeding water can readily be detected. This is achieved by a passivation measurement on a reference steel surface.

The advantage of the invention is that, by means of a simple passivation measurement in critical zones, where a sensor is installed, it can be determined during the injection operation whether the duct is filled with passivating mixture. In this way corrections can be made during the injection procedure. The passivation measurement makes it possible to verify that both the pH of the mixture as well as its chloride content enable passivity of the prestressing steel. It is thereby possible to verify comprehensive corrosion protection, both with respect to filling as well as with respect to mixture composition. The sensor is of simple construction, and can be integrated with minimal effort in all critical zones of the tendon.

BRIEF DESCRIPTION OF DRAWINGS

The invention will be better understood from reading the following description, given by way of non-limiting example, with reference to the attached drawings.

MODES FOR CARRYING OUT THE INVENTION

Figure 1A:
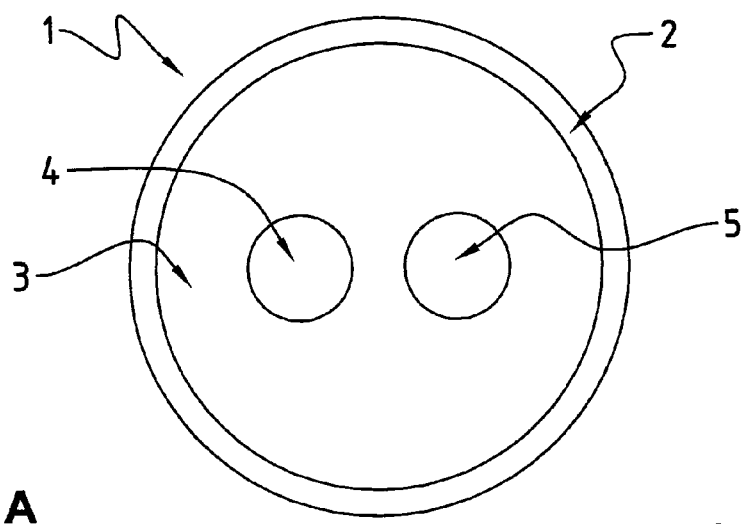
FIG. 1A shows a front view of a sensor for detecting the filling with mixture and the passivating properties of the mixture.

Referring to the drawings (FIG. 3), one sees a tendon 100 used for the construction of prestressed, suspended and stayed structures (these structures are not represented), such as suspension bridges, cable-stayed bridges, stadium roofs, buildings, telecommunications towers, post-tensioned bridges, containment structures, etc.

The tendon 100 comprises a plurality of strands 10 embedded in a medium made up of a material capable of hardening, e.g. a mixture 11 containing at least two components such as cement and water. This mixture 11 is known by the term grout. Each tendon 100 comprises a plurality of strands 10 which are made up of steel.

The tendon 100 also comprises an encasing tube 12, in which the strands 10 of the tendon 100 are introduced before the mixture 11 is poured in the encasing tube 12 in such a manner as to completely fill a hollow space 110 situated between the individual strands and/or between the strands and the encasing tube 12. The encasing tube 12 has a wall which can act as a mould, and which can be considered as constituting a vessel.

The filling mixture namely ensures that the strands are in contact along their entire length with the alkaline pore solution of the mixture 11.

The invention relates to a method for determining the passivating properties of the mixture 11. This method for determining the passivating properties of a mixture 11 containing at least two components, which are cement and water, includes the steps of:
taking three elements, each made up of an electrically conductive material, these elements being referred to as first electrode 2, second electrode 4 and third electrode 5,
fixing at least one of these three elements on a support 3 in such a manner that
they are electrically insulated reciprocally, and
the mixture 11 is able to come into contact with at least one predetermined face situated on each electrode, these faces being referred to as first face 20, second face 40 and third face 50,
selecting the first electrode 2 and the third electrode 5 and applying between these two electrodes
a direct current, referred to as first direct current, of predetermined polarity, referred to as first polarity, resulting in electrolytic reactions on the third electrode 5, for a predetermined duration D1, referred to as first duration D1, and then
selecting the second electrode 4 and the third electrode 5, and
measuring the voltage V between these two electrodes during said first predetermined duration D1, and
storing the measurement for the variation of said voltage V during said first predetermined duration D1,
comparing the variations in the voltage V between the second electrode 4 and the third electrode 5 during the first predetermined duration D1, with predetermined data defining at least whether or not a mixture 11 has passivating properties, and
determining at least whether or not the mixture 11 has such passivating properties.

The electrolytic reactions on the third electrode 5 are anodic reactions.

The invention moreover relates to a sensor 1 designed to implement the invention. This sensor 1 has three elements, each made up of an electrically conductive material, these elements being said first electrode 2, second electrode 4 and third electrode 5, and at least one of these three elements is fixed on a support 3 in such a manner that these elements are electrically insulated reciprocally.

Using an electrically insulating material as a support 3, a second electrode 4, made up of an electrically conductive material, and a third electrode 5, made of steel, are installed in an electrically conducting first electrode 2, made up of a tubular part. The first electrode 2, the second electrode 4 and the third electrode 5 are electrically connected by means of a multi-core cable 6.

The first electrode 2 and the second electrode 4 are composed ideally of stainless steel. Used as electrically insulating material is e.g. polytetrafluoroethylene, polyethylene or epoxy resin.

Figure 2:
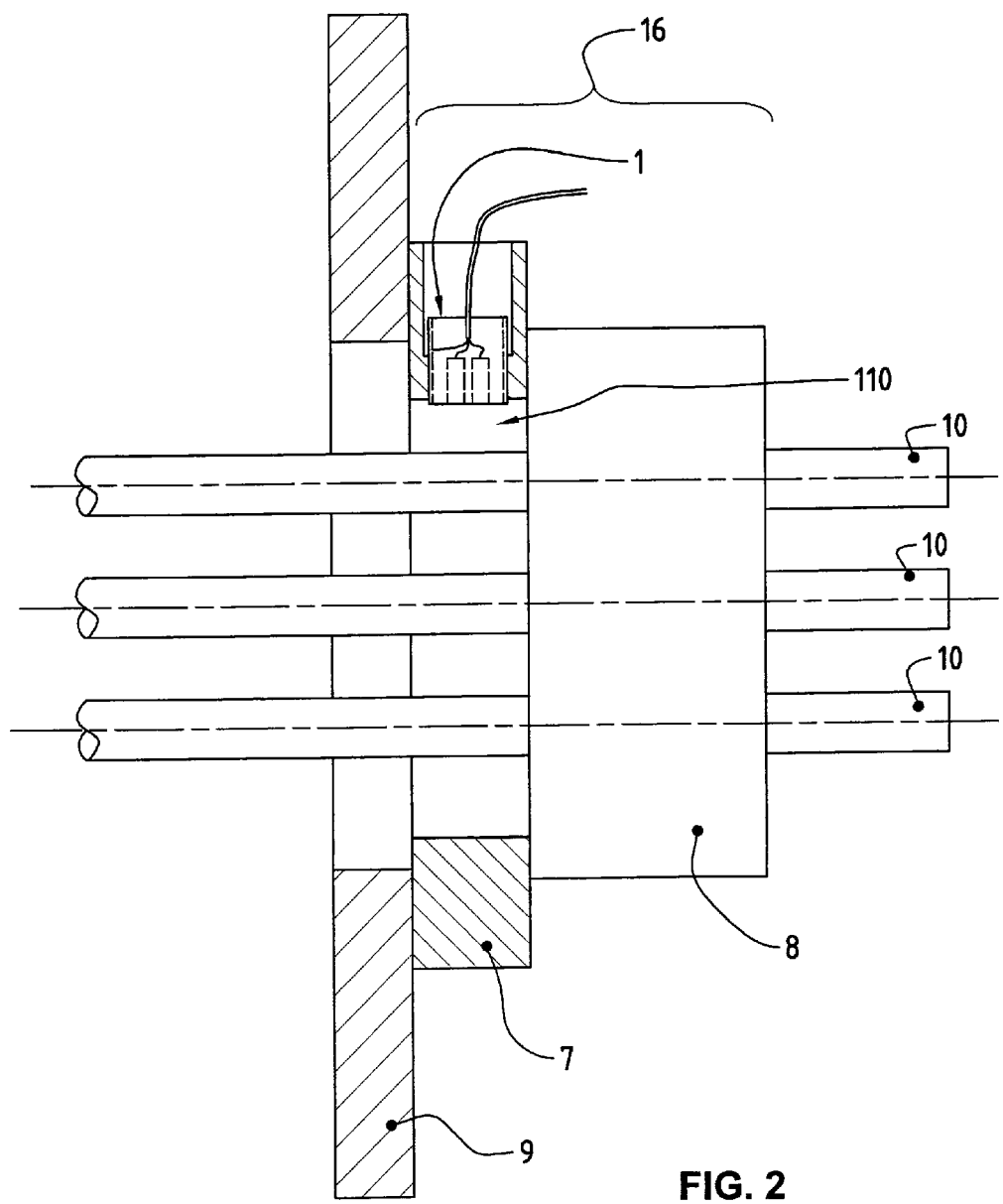
FIG. 2 shows the sensor after integration in the anchorage.

As shown in FIG. 2, the sensor 1 can be integrated in an anchoring device 16 (anchorage). As represented, clamped between a bearing plate 9 and an anchor head 8 is a force distribution ring 7. The sensor 1 is integrated in this force distribution ring 7. Ideally, the sensor 1 is installed by means of a screw into said force distribution ring 7. The force distribution ring 7 has a large aperture in which the strands are spaced, and these strands have to be embedded with a mixture 11.

The force distribution ring 7 has a wall which can be considered as constituting a vessel in which the mixture 11 can be poured in order to completely fill a hollow space situated between the strands and the distribution ring 7.

Figure 3:
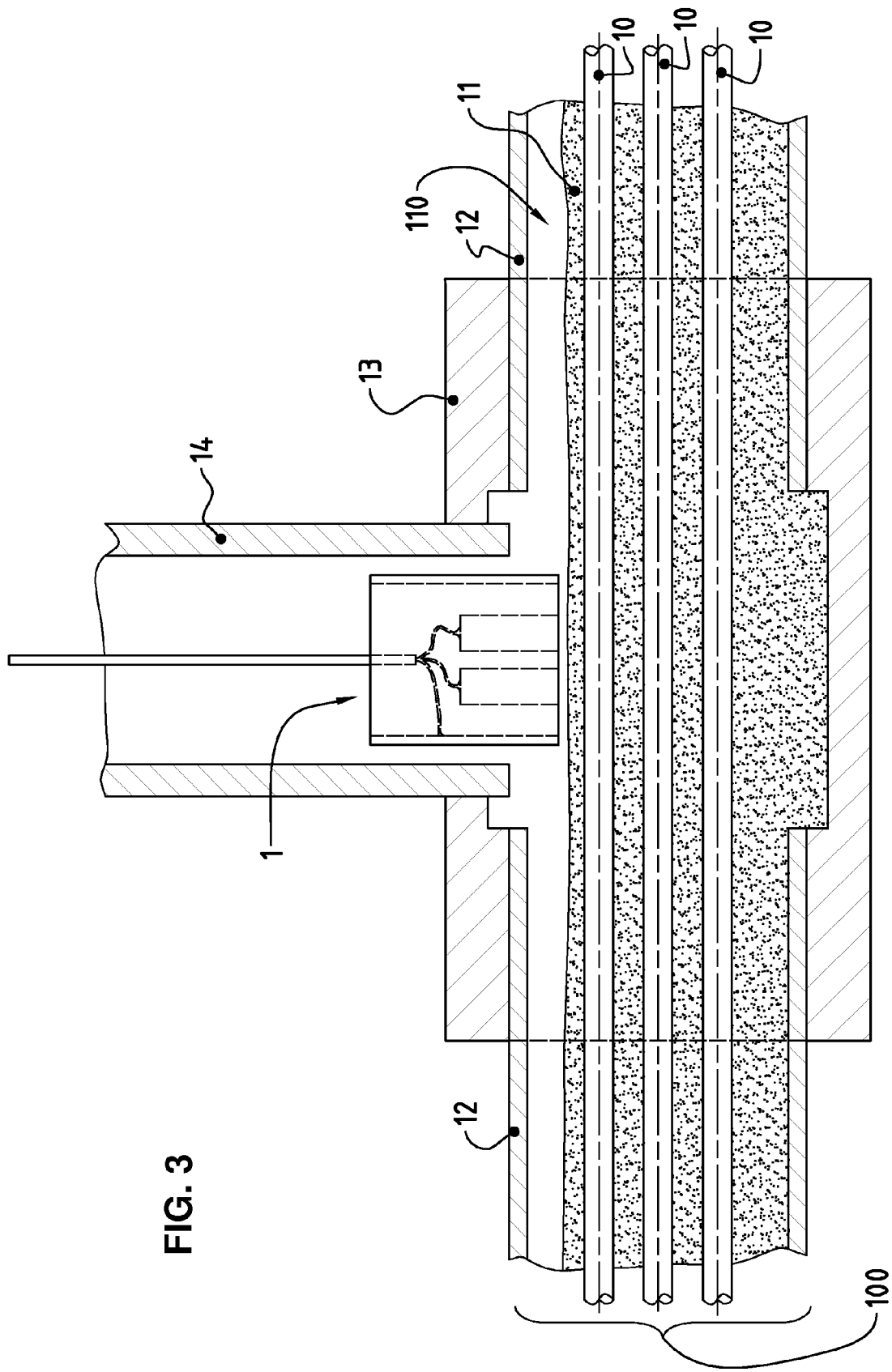
FIG. 3 shows the sensor after integration in an encasing tube.

As shown in FIG. 3, the sensor 1 can be mounted in an encasing tube 12 at a place where a ventilation tube 14 is fixed, in such a manner that the mixture 11 comes into contact with said sensor 1. Preferably, the sensor 1 is integrated in the ventilation tube 14 in such a manner that it does not stop the exit of air. Alternatively, the sensor may be installed into a similar tube which however, is not used for ventilation.

The steps of comparing the variations in the voltage V between the second electrode 4 and the third electrode 5 during the first predetermined duration D1, with predetermined data defining at least whether or not a mixture 11 has passivating properties, and determining at least whether or not the mixture 11 has such passivating properties, comprises at least:
a) checking whether the difference, referred to as first voltage difference V1, between the maximum voltage value of the first predetermined duration 01 and the voltage value at a first predetermined instant T1 of the first predetermined duration 01, exceeds a first predetermined voltage value or not.
Preferably:
before said first direct current of first predetermined polarity, is applied between the first electrode 2 and the third electrode 5, for a first period of first predetermined duration D1,
another direct current, referred to as second direct current, of predetermined polarity, referred to as second polarity, opposed to the first polarity, is applied between the first electrode 2 and the third electrode 5, for a predetermined duration D2, referred to as second duration D2, when the voltage V between the second electrode 4 and the third electrode 5 has been measured during said first predetermined duration D1,
the voltage V between the second electrode 4 and the third electrode 5 is measured during said second predetermined duration D2 and then these voltage values are stored,
when comparing the variations in the voltage V between the second electrode 4 and the third electrode 5 during the first predetermined duration D1, with predetermined data defining at least whether or not a mixture has passivating properties, and determining at least whether or not the mixture 11 has such passivating properties,
the variations are also compared in the voltage V between the second electrode 4 and the third electrode 5 during said second predetermined duration 02.

In this case, the step of selecting the first electrode 2 and the third electrode 5 and applying a first direct current and then a second direct current between these two electrodes involves the use of a first direct current and a second direct current with:
a first predetermined polarity and a second predetermined polarity that are opposite,
a first duration D1 and a second duration D2 that are equal.

In a preferable manner:
the first predetermined duration D1 is of ten seconds (10 s), and/or
the second predetermined duration D2 is of ten seconds (10 s).

Anodic polarization states occur during the first predetermined duration D1, and cathodic polarization states during the second predetermined duration D2.

Preferably, the steps of comparing the variations in the voltage V between the second electrode 4 and the third electrode 5 during the first predetermined duration D1 and the second predetermined duration D2, with predetermined data defining at least whether or not a mixture 11 has passivating properties, and determining at least whether or not the mixture 11 has such passivating properties, comprises:
a) checking whether the difference, referred to as first voltage difference V1, between the maximum voltage value of the first predetermined duration D1 and the voltage value at a predetermined instant T1, referred to as first instant T1, of the first predetermined duration D1, exceeds a first predetermined voltage value, or not, and
b) checking whether the difference, referred to as second voltage difference V2, between the maximum voltage value of the first predetermined duration D1 and the voltage value at a predetermined instant T2, referred to as second instant T2, of the second predetermined duration D2, is within a first predetermined range, or not, and
c) checking whether the difference, referred to as third voltage difference V3, between the voltage value at a predetermined instant T3, referred to as third instant T3, of the first predetermined duration D1 and the voltage V at a predetermined instant T4, referred to as fourth instant, of the second predetermined duration D2 is within a second predetermined range, or not.

Preferably at least one of these two conditions is satisfied:
at least one of the first predetermined instant T1 and the fourth predetermined instant T4 is between ten percent and one hundred percent of the value of the first predetermined duration D1, and
at least one of the second predetermined instant T2 and the third predetermined instant T3 is between ten percent and one hundred percent of the value of the second predetermined duration D2.

The value of the first predetermined duration D1 is between one second and thirty seconds, and/or the value of the second predetermined duration D2 is between one second and thirty seconds.

Preferably at least one of these two conditions is satisfied:
at least one of the first predetermined instant T1 and the fourth predetermined instant T4 is equal to ninety percent of the value of the first predetermined duration D1, and
at least one of the second predetermined instant T2 and the third predetermined instant T3 is equal to ninety percent of the value of the second predetermined duration D2.

According to the invention, for the step of selecting the first electrode 2 and the third electrode 5 and applying between these two electrodes
a first direct current of first predetermined polarity, for a first predetermined duration D1, and then
a second direct current of second polarity opposed to the first polarity, for a second predetermined duration D2:
the first direct current is such that a density of current of two point five milliampere per square centimeter (2.5 mA/cm$^2$) emerges from the third electrode 5, and
the second direct current is such that a density of current of two point five milliampere per square centimeter (2.5 mA/cm$^2$) emerges from the first electrode 2.

Preferably, for the step of comparing the variations in the voltage V between the second electrode 4 and the third electrode 5 with predetermined data defining at least whether or not a mixture has passivating properties, when:
the first voltage difference V1 is a maximum of fifty millivolts (50 mV) (first predetermined voltage value),
the second voltage difference V2 is one point eight volts to two point three volts (1.8 V to 2.3 V) (first predetermined range), and
the third voltage difference V3 is one point eight volts to two point three volts (1.8 V to 2.3 V) (second predetermined range),
the conclusion is that the mixture 11 has passivating properties, at least in the vicinity of the three electrodes.

It is easy to understand that the method of the invention also indirectly allows checking the filling of an encasing tube with the aforementioned mixture, at least in the vicinity of the three electrodes.

In the step of comparing the variations in the voltage V between the second electrode 4 and the third electrode 5 with predetermined data defining at least whether or not a mixture 11 has passivating properties, when the change in potential between
the fourth second of at least the first predetermined duration D1 and second D2 predetermined duration, and
the ninth second of at least the first predetermined duration D1 and second D2 predetermined duration is more than six millivolts (6 mV),
the conclusion is that the third electrode 5 is in contact with a mixture 11 made up of hardening cement and water, instead of only bleed water, that is to say liquid emerging from a mixture 11 of water and cement.

Preferably, the step consisting of taking three elements, each made up of an electrically conductive material, these elements being said first electrode 2, second electrode 4 and third electrode 5, each of these three electrodes having at least one face 20, 40, 50, comprises the operation of selecting three elements each made up of steel.

Figure 4:
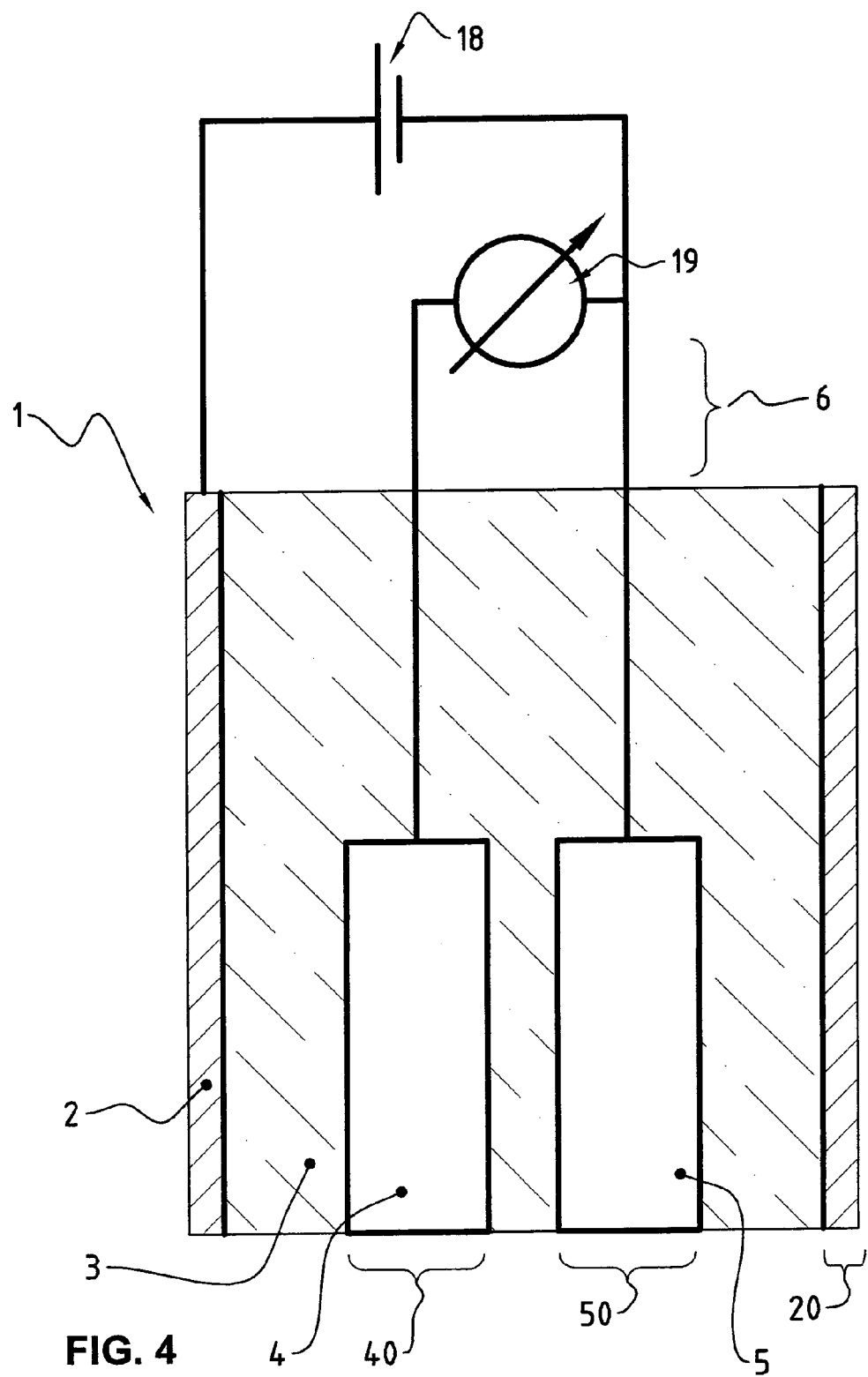
FIG. 4 shows the measuring setup for the passivation measurement.

Shown in FIG. 4 is a measuring setup for the passivation measurement. By means of a power source 18, such as e.g. a battery or a galvanostat, a current is impressed between the first electrode 2 and the third electrode 5. With a voltage measuring device 19, such as e.g. a voltmeter, the voltage V is measured between the third electrode 5 and the second electrode 4.

Figure 5:
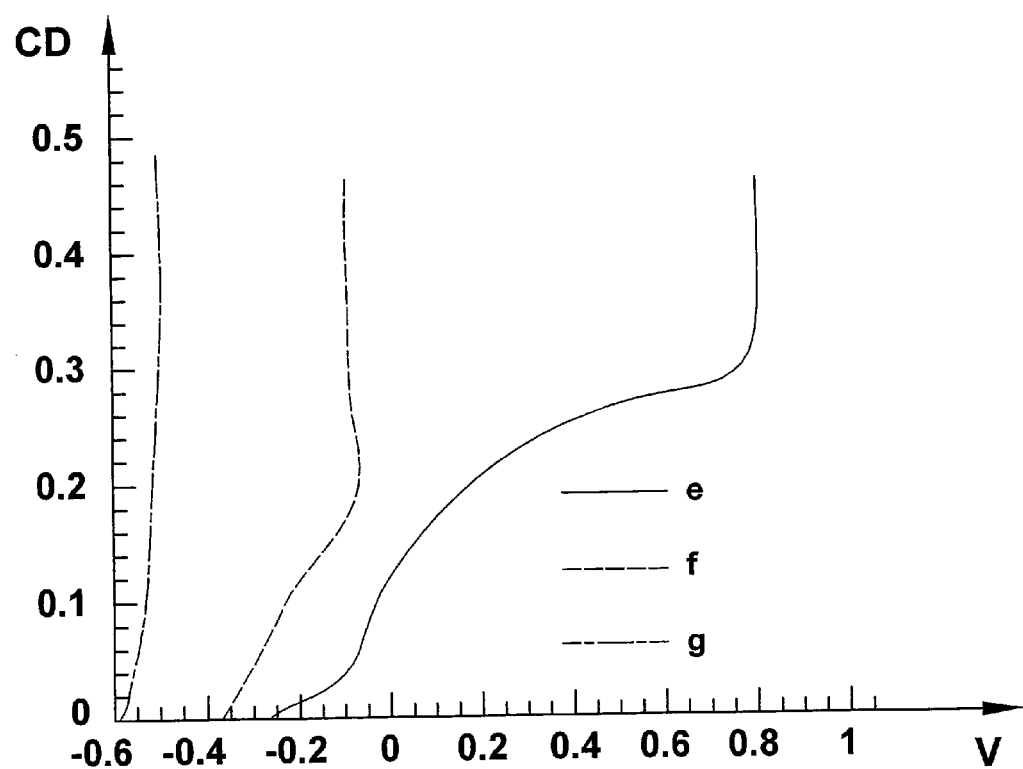
FIG. 5 shows a measurement example of a passivation measurement for different mixture materials.

The result of this measurement for various media in contact with the sensor 1 is represented in FIG. 5. Shown on the horizontal axis is the voltage V (volts) between the second electrode 4 and the third electrode 5, and shown on the vertical axis is the current density CD emerging from the third electrode 5 (mA/cm$^2$).

For a filling of the hollow space 120 with a mixture 11 of a passivating chloride-free alkaline type (curve "e"), a maximal voltage is achieved through the current flow, which maximal voltage is limited by the development of oxygen. The increase in the third electrode 5 compared with the second electrode 4, in this case composed of stainless steel, to a value higher than 0.5 volt indicates efficient passivation.

If the hollow space 120 is filled with diluted bleed water (curve "f"), the measurable voltage V increase under flow of current is significantly lower. The value of 0.5 volt is not surpassed. This indicates the triggering of corrosion owing to too low an alkalinity.

In the case of a filling of the hollow space 120 with tap water, a very negative voltage V is even measured (curve "g"). This indicates extensive corrosion of the steel of the strands.

The procedure shown in FIG. 5 exhibits the disadvantage that the measurement of the potential of the third electrode 5 to the stainless steel electrode 4 is influenced by the oxygen content in the mixture 11 and the passivation quality of the second electrode 4.

Moreover, the presence of a passive film on the third electrode 5 from a previous exposure to a passivating environment may result in misleading results indicating passivity even in an aggressive environment.

Figure 6:
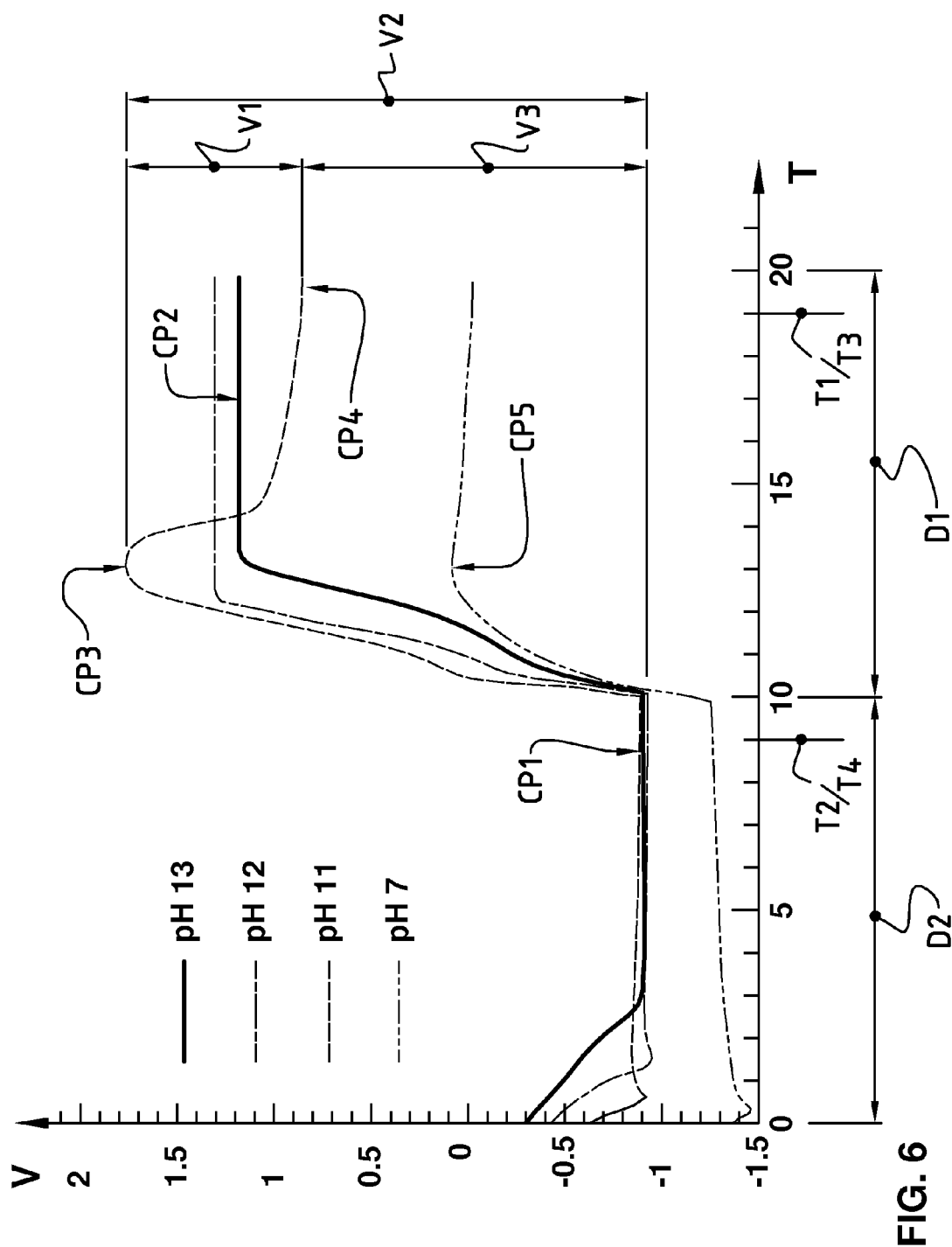
FIG. 6 shows a measurement example of a passivation measurement for different pH values over time T.

These problems are overcome by the above-mentioned method, as shown in FIG. 6 for different pH values.

As mentioned in the foregoing, the passive film possibly formed on the third surface 50 of third electrode 5 is removed by cathodic polarization (second direct current of second polarity, for a second predetermined duration D2=e.g. 10 seconds by a current of −2.5 mA/cm$^2$). The current is impressed between the first electrode 2 and the third electrode 5.

A new passive film develops on the third surface 50 of the third electrode 5 through the application of an anodic current between the third electrode 5 and the first electrode 2 (first direct current of first predetermined polarity opposed to the second polarity for a first predetermined duration D1=e.g. 10 seconds by a current of +2.5 mA/cm$^2$).

During the measurement, the alkalinity changes owing to the hydrogen and oxygen development taking place on the third surface 50 of third electrode 5. This effect can be minimized if the amount of charge during the cathodic and anodic polarization is equal.

This is the case if the cathodic polarization lasts for ten seconds at minus two point five mA/cm$^2$ (−2.5 mA/cm$^2$) and the anodic polarization lasts for 10 seconds at plus two point five mA/cm$^2$ (+2.5 mA/cm$^2$). As a consequence, repeated measurements result in minimal interference with the pH of the mixture 11.

Shown in FIG. 6 are the electrochemical processes taking place on the third surface 50 of third electrode 5. Starting with an undefined third surface 50 with possible oxide and passive film coverage, a cathodic polarization (first curve part CP1) reduces all residual protective passive film.

A subsequent anodic polarization will result in the formation of a protective passive film if the pH value is sufficiently high and the chloride content sufficiently low (second curve part CP2). This is the case for pH values equal to twelve or higher than twelve (pH 12, pH 13).

If the pH value of the mixture 11 is too low (e.g. pH 11) or the chloride content too high, formation of a passive film may take place (third curve part CP3); however, the subsequent polarization can cause the partial failure of the passive film resulting in corrosion activation and a drop in potential (fourth curve part CP4).

If the pH value of the mixture 11 is very low (e.g. pH 7), no formation of a passive film will take place at all (fifth curve part CP5).

The decision about the activation of corrosion is possible based on the potential difference between the second electrode 4 and the third electrode 5. Although the second electrode 4 is not a stable reference electrode with a well defined potential value, the passivation measurement is very reliable. This is owing to the fact that the decision about the activation of corrosion is possible based on a potential decrease during the anodic polarization between third curve part CP3 and fourth curve part CP4 and/or based on the difference between first curve part CP1 and fifth curve part CP5.

Since the decision about the activation of corrosion is based on the difference between two potential readings, the possible error in relation to the second electrode 4 is eliminated.

The procedure shown in FIG. 6 uses in addition hydrogen development during a cathodic polarization (first curve part CP1) and/or oxygen development during anodic polarization (second curve part CP2) to determine the effect of the potential of the second electrode 4 and to estimate the effect of the ohmic potential drop in the mixture 11.

Since the potential difference between the oxygen and hydrogen development in alkaline mixture 11 is roughly around two volts, the difference between these two potentials can be used as a criterion for evaluating the wetting of the third electrode 5 with a mixture 11 having passivating properties.

Based on the examples shown, the following criteria can be used to determine the presence of a passivating mixture 11 on the surface of the sensor 1:

a) The difference between the maximum potential during an anodic polarization (second curve part CP2, third curve part CP3, fifth curve part CP5) and the potential after a defined time during anodic polarization (second curve part CP2, fourth curve part CP4, fifth curve part CP5) (T1: e.g. 9 seconds) may not exceed a certain value (e.g. 50 mV), b) The difference between the maximum potential in anodic polarization (second curve part CP2, third curve part CP3, fifth curve part CP5) and the potential after a defined time during cathodic polarization (first curve part CP1) (T2: e.g. nine seconds) must be within a certain range (e.g. one point eight and two point three volts), c) The difference between the potential after a defined time during anodic polarization (second curve part CP2, third curve part CP3, fifth curve part CP5) (T3: e.g. nine seconds) and the potential after a defined time during cathodic polarization (first curve part CP1) (T4: e.g. nine seconds) must be within a certain range (e.g. one point eight and two point three volts).

The above-mentioned conditions "a", "b" and "c" make it possible to eliminate the effect of possible potential fluctuations of the second electrode 4.

Moreover they take into account the ohmic potential drop in the mixture 11, which can influence the measurement as well. Investigating various parameters, it was shown that a most reliable determination of the wetting of the sensor 1 with mixture 11 having passivating properties can be achieved through a combination of the conditions "a" and "b". However, also condition "c" or "a" alone allows determination of the wetting of the surfaces of the sensor with a mixture 11 having passivating properties.

Figure 7:
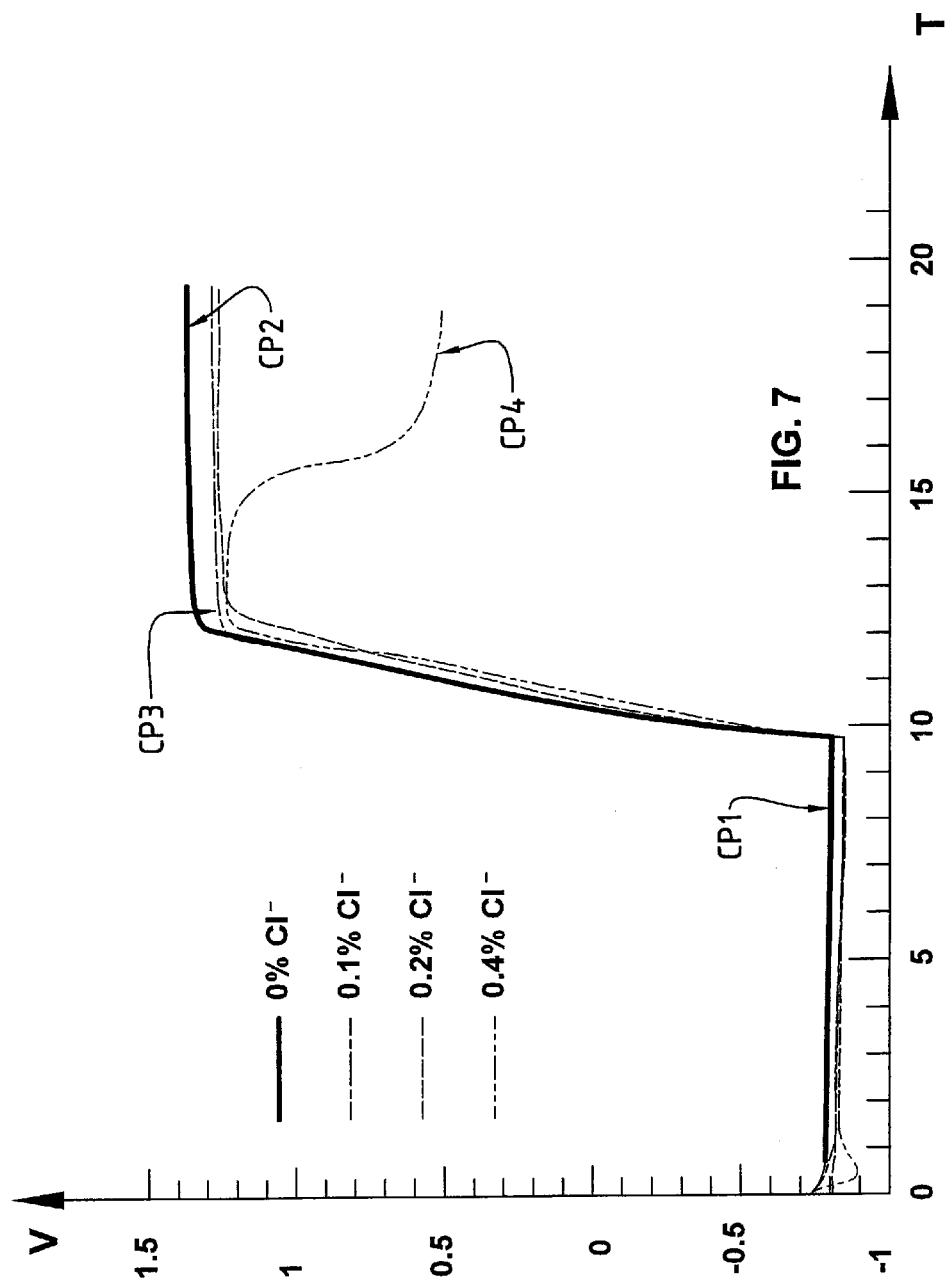
FIG. 7 shows an example of a passivation measurement for different chloride contents of the mixture over time T.

In FIG. 7, the corresponding measurement is shown for a typical mixture 11 with different chloride contents. The difference between the maximum potential and the potential after nine seconds in anodic polarization is zero for zero point one and zero point two % Cl-(chloride), demonstrating the passivating properties of the mixture 11.

In contrast, this difference is about seven hundred and fifty mV for zero point four % Cl-(chloride), demonstrating the activation of corrosion.

The determination of the difference between the maximum potential in anodic polarization and the potential after a defined time during cathodic polarization (first curve part CP1) (e.g. nine seconds) allows determination of the ohmic potential drop in the mixture 11.

Since the ohmic potential drop will increase, once the mixture 11 starts to set, monitoring of the potential drop over time can be used to determine whether the sensor 1 is in contact with a hardening mixture 11 having passivating properties or only with bleed water having passivating properties.

This procedure requires the measurement of the ohmic potential drop in the mixture 11 after at least twenty-four hours after the injection of the mixture 11 in the encasing tube 12.

If the reading indicates the presence of bleed water, the problem can no longer be corrected. Therefore it would be most helpful if the decision about the presence of bleed water could be made based on a measurement taken directly after injection of the mixture 11, when it is still possible to correct the situation through additional injection.

The invention makes such a decision possible using the electrochemical processes involved. During cathodic polarization not only are residual oxide layers removed, but also hydrogen development takes place and the pH value of the mixture 11 increases.

On the other hand, the anodic polarization will not only result in the formation of a passive film, but also in oxygen development and decrease in the pH value of the mixture 11. The potential for oxygen and hydrogen development are dependent on the pH value according to the Nernst equation.

As a consequence, the potential will change with increasing polarization time, during both the anodic and cathodic polarization. Since the rate of pH change is defined by the applied current density CD, the potential change should always be identical for all tests.

The pH change, however, is not only influenced by the amount of hydroxide or hydrogen ions produced, but also by their accumulation on the front of the third electrode 5. As a consequence, the pH value will change fast if a mixture 11 with passivating properties is present in contact with the third electrode 5.

If, on the other hand, bleed water is in contact with the third electrode 5, the convection and the high diffusion rate in the liquid will prevent the accumulation of the hydroxide or hydrogen ions. As a consequence, the change in pH value will be smaller, and the change in potential will be smaller too. The monitoring of the potential over time allows, therefore, determining the accumulation of reaction products (hydrogen or hydroxide ions) in contact with the third electrode 5.

Figure 8:
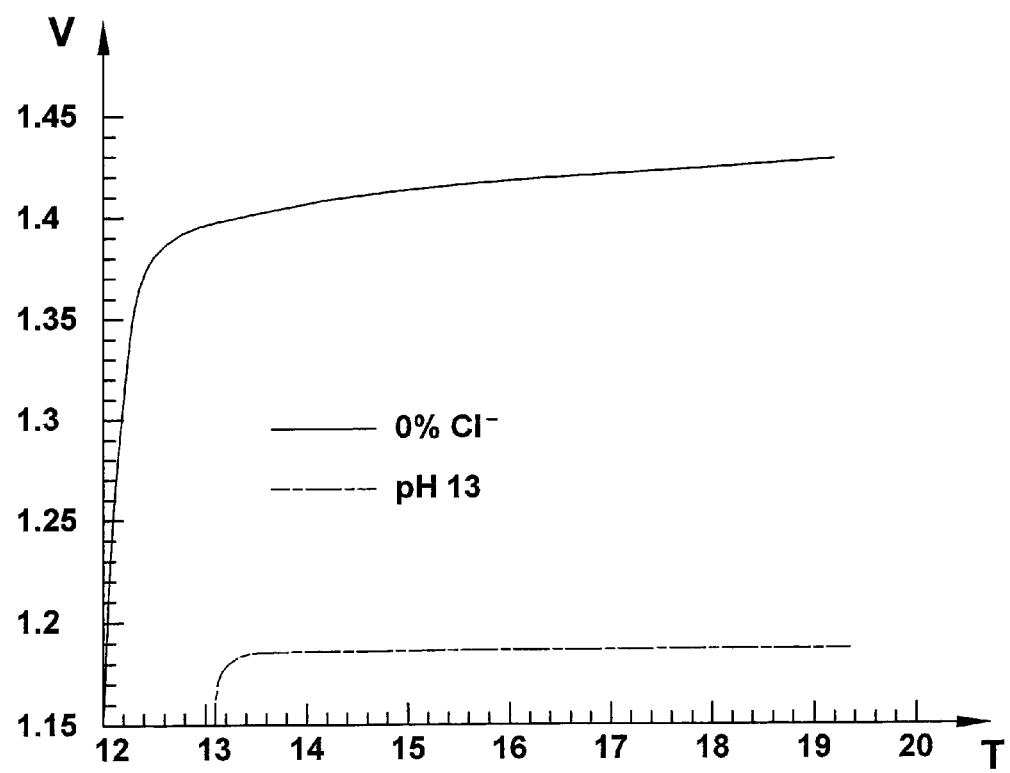
FIG. 8 shows measurement data of FIG. 6 and FIG. 7 over time T.

This effect is illustrated in FIG. 8, where the results of FIG. 5, pH thirteen (pH 13), and FIG. 7, zero % Cl-(chloride), are compared. While the potential remains more or less constant in the electrolyte with pH thirteen (pH 13) after the maximum value is reached, a continuous increase is observed for the mixture 11 with zero % Cl-(chloride).

Under the given measurement conditions, the increase in potential during second fourteen and twenty of the anodic polarization should be at least six mV if mixture 11 with passivating properties is present in contact with the third electrode 5. This effect will increase with the hardening of the mixture 11, since the transport of the reaction products (hydroxide ions during cathodic polarization and hydrogen ions during the anodic polarization) gets slower in the solid mixture.

This very same effect can be used in later investigations for determination of the pH value on the third electrode 5. During anodic polarization, the alkalinity of the mixture 11 in contact with the third electrode 5 will decrease with ongoing polarization. At a constant anodic polarization current, the change in pH will occur more quickly when the starting pH value was lower, since fewer neutralizing hydroxide ions were available. Hence the potential drop over time will be greater in a low pH value environment. If the pH value in the mixture 11 is high, the same current over time creates a smaller change in pH value, and a smaller change in potential is measured.

This procedure allows determining the pH value in front of the third electrode 5, provided that the diffusion rate for the produced hydrogen ions and the neutralizing hydroxide ions in the mixture 11 is constant over time, or known. If the current is applied in a way that the overall charge is zero after the entire test, the pH changes introduced can be compensated.

In the example shown, the decision about the passivating properties of the mixture 11 was based on a ten-second anodic polarization. Alternatively, it is possible instead to continue the anodic polarization until corrosion activation takes place and a decrease in potential is observed. This effect will occur since the pH value will decrease over time owing to the production of hydrogen ions in anodic polarization. Therefore, the ratio between chloride ions and hydroxide ions will decrease over time, and activation will take place. This procedure allows getting quantitative information about the passivating properties of the mixture 11 instead of just pass/fail information. A more detailed analysis of the chloride content is possible, based on this procedure.

Use of the sensor 1 thus makes possible a comprehensive guarantee of the corrosion protection of tendons. The sensor 1 can be simply integrated at all critical areas in the anchorage and in the encasing tube 12, and, by means of a simple passivation measurement, enables checking the filling during the step of injection with the corrosion-protection mixture 11.

In the event of flaws or errors, steps can thus be directly taken during the injection, and the mixture 11 can be replaced again. In contrast to alternative methods, such as monitoring through radar or visual inspection, the filling of the encasing tube 12 is checked directly during the injection. Above and beyond this, possible for the first time is a direct monitoring of the corrosion protection effect of the mixture 11, using the sensor 1. This measurement is so quick and uncomplicated that it can be done upon completion of the injection. Thus it is possible to take steps, if necessary, before the setting of the mixture 11.

Different variants of the procedure are conceivable. For example, each sensor 1 can be equipped with a measuring device that continuously measures the passivating properties and sends the data to a central station at the injection pump. The personnel can thereby follow the position of the front end of the mixture 11 in the encasing tube 12 during the injection.

In addition, there exists the possibility of transmitting these data via a wireless network to an independent station which carries out the logging of the complete injection operation for the builder.

The passivation measurement shown can also be carried out by hand using a simple battery and a voltmeter. A simple current pulse of predetermined duration can thereby be used.

This can take place through interruption of the current. Using this simple battery-driven device, the measurement can also be carried out at the same time based on current and voltage V. Measurement of the grouting mixture and of the corrosion protective effect is thereby possible in one operation.

Furthermore there exists the possibility of running the electrical connections of all sensors 1 or of selected sensors 1 into a central measuring box, and using them for later monitoring measurements. The design also permits application of other methods such as impedance spectroscopy, galvanostatic pulse measurement, determination of the linear polarization resistance and potential and corrosion current measurement.

Moreover in the case of a connection to the tendon, as exists in the situation in FIG. 2, for example, measurements directly on the tendon 10 are possible. The sensor 1 thus enables not only comprehensive and direct quality control during the injection operation, it also offers the possibility of long-term corrosion monitoring of the tendon 10.

The sensors 1 can thereby be integrated directly into a comprehensive monitoring system of the structure. The voltage V between the second electrode 4 and the third electrode 5 can thus be captured as a function of time. With the onset of corrosion, the voltage V will decrease. Alternatively, the current between the third electrode 5 and the ring 2 can be measured as a function of time. With an increase in the current, conclusions can likewise be drawn regarding corrosion onset and even rate of corrosion. Moreover, the voltage between the strands 10 and the second electrode 4 can be measured.

Additionally, the sensor 1 may be used to judge the effect of the cathodic protection on the potential distribution on the tendon. The polarization of the strand 10 can be determined by measuring the potential between the second electrode 4 and the strand 10. Simultaneously the cathodic current density on the third electrode 5 can be determined allowing estimation of the level of cathodic protection. This possibility is especially relevant for electrically insulated tendons.

The invention is of course not limited to the embodiment example shown and described. Thus the sensor 1 can contain further electrodes, so that the passivation measurement can run on independent electrodes.

Instead of the first electrode 2, any other third electrode 5 in the sensor 1 can be used. It is also possible to use a contact in the reinforcement of the concrete structure instead of the first electrode 2 or second electrode 4. This is possible, since the reinforcement is typically in contact with the bearing plate, the anchor head and the strands. Additionally it is possible to combine first electrode 2 and second electrode 4 in one electrode. This is especially possible if the surface of the combined electrode is large. Therefore the reinforcement or the strands or the anchor head would be suitable as a combined electrode for this application.

The material of the second electrode 4, the third electrode 5 and the first electrode 2 has to show electrical conductivity. Thus copper, graphite, carbon-fiber-reinforced plastic, a plastic filled with any electrically conductive material, or any other metal can be used instead of stainless steel, for example. For the passivation measurement, it is essential that the third electrode 5 be composed of an iron-based material having as similar as possible a passivation behavior as the strands. Use of steel or use of steel prestressing strands is obvious. Using iron is also conceivable, however.

Figure 1B:
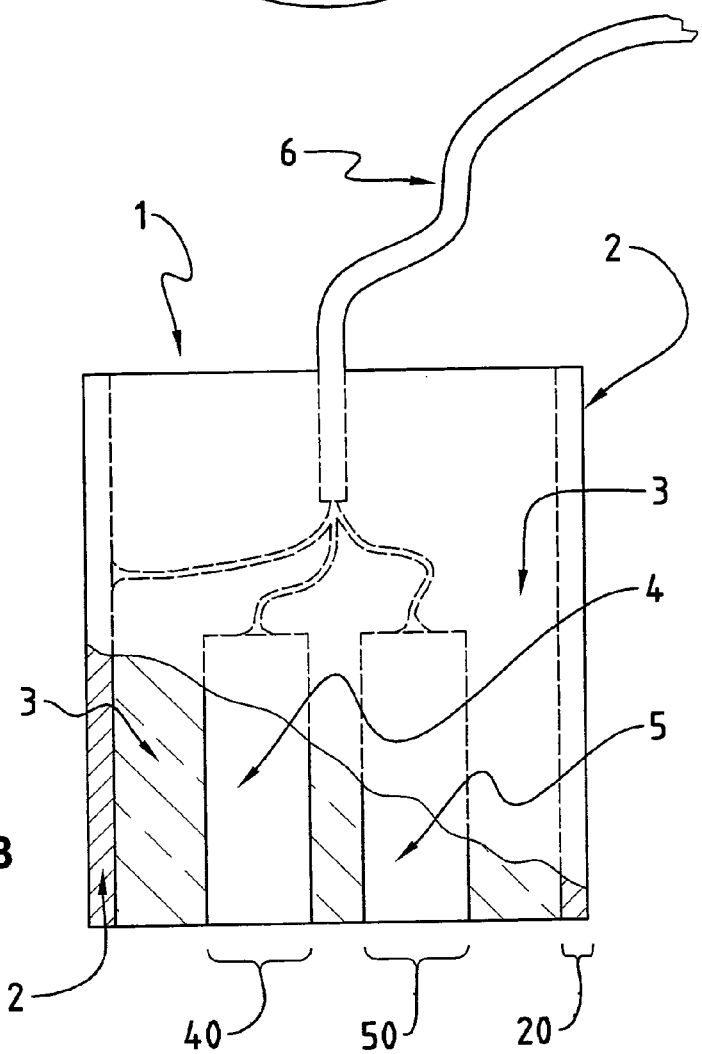
FIG. 1B shows a side view of a sensor for detecting the filling with mixture and the passivating properties of the mixture.

If the detection of the presence of mixture 11 with passivating properties instead of bleed water or the determination of the pH value at later stages is the only information of interest, the material of third electrode 5 can be of any electrically conductive material. For anodic polarization, it is preferably an inert or passive material, such as gold, platinum, graphite titanium, tantalum, etc. There are no limitations regarding the geometry of the electrode. It can have any shape as shown in FIG. 1. It is important to note that it does not have to exhibit a planar shape.

For example, a cylindrical geometry may also be used. Additionally it is possible to segment the third electrode 5 into several single electrodes which are located in the same area or which are spread out. For example it is possible to introduce several individual third electrodes 5 in the same force distribution ring 7. In one single measurement, several areas would be tested. It is even possible to extend the third electrode 5 over the entire encasing tube 12. This electrode could be split in single individual electrodes. This could be achieved by using a wire that is insulated and that is introduced parallel to the prestressing strands. By removing the insulation in the critical areas or at regular intervals, the information about the filling of the entire encasing tube 12 with mixture 11 with passivating properties could be obtained in a single measurement. For example, a prestressing strand coated with polyethylene could be used. Wherever the presence of mixture 11 has to be confirmed, the polyethylene has to be removed prior to insertion into the encasing tube 12.

The current does not have to be constant during the test. Any possible waveform can be used, such as a ramp or a sinus wave including the positive and negative half wave. However, the use of a constant current results in easy interpretation of the results.

Since the second electrode 4 is not carrying any current, its conductivity is not critical. Its only function is to exhibit a stable potential during the time of the measurement. As a consequence, not only the materials listed for the third electrode 5, but also organic and inorganic semiconductors, or even polymer-coated metals and semiconductors may be used.

There exists furthermore the possibility of integrating a reference electrode into the sensor 1 in order to be able to measure the absolute electrochemical potential. In this case, the voltage V measurement would take place between the reference electrode and the third electrode 5. Exact determination of the pH value of the mixture 11 would thereby be feasible.

The invention can also be applied to the monitoring of the passivation properties and pH value of other concretes or mixtures 11 used in concrete structures.

According to the invention the change in potential in the solid mixture is used to determine the alkalinity of the mixture 11 at any later point in time.

According to the invention the measuring of the potential polarization resistance of the second electrode 4 is used for monitoring of the corrosion behavior over time.

The invention claimed is:

1. A method of determining the passivating properties of a mixture (11) containing at lest two components, which are cement and water, including the steps of:
   taking three elements, each made up of an electrically conductive material, these elements being referred to as first electrode (2), second electrode (4) and third electrode (5), fixing at least one of these three electrodes on a support (3) in such a manner that
they are electrically insulated reciprocally, and
the mixture (11) is able to come in contact with at least one predetermined face situated on each electrode, these faces being referred to as first face (20), second face (40) and third face (50),
selecting the first electrode (2) and the third electrode (5) and applying between these two electrodes,
a direct current, referred to as first direct current, of predetermined intensity value, referred to as first intensity value, and predetermined polarity, referred to as first polarity, resulting in electrolytic reactions on the third electrode (5) for a predetermined duration (D1), referred to as first duration, and then
selecting the second electrode (4) and the third electrode (5), and
measuring the voltage (V) between these two electrodes during said first predetermined duration (D1), and
storing the measurement for the variation of said voltage (V) during said first predetermined duration (D1),
comparing the variations in the voltage (V) between the second electrode (4) and the third electrode (5) during the first predetermined duration (D1), with predetermined data defining at least whether or not a mixture (11) has passivating properties, and
determining at least whether or not the mixture (11) has such passivating properties.

2. The method according to claim 1, characterized in that the steps of comparing the variations in the voltage (V0 between the second electrode (4) and the third electrode (5) during the first predetermined duration (D1), with predetermined data defining at least whether or not a mixture (11) has passivating properties, and determining at least whether or not the mixture (11) has such passivating properties, consists at least in:
a) checking whether the difference, said first voltage difference (V1), between the maximum voltage value of the first predetermined duration (D1) and the voltage value at a first predetermined instant (T1) of the first predetermined duration (D1), exceeds a first predetermined voltage value or not.

3. The method according to claim 1, characterized in that it further comprises the steps of:
before said first direct current of first predetermined polarity, is applied between the first electrode (2) and the third electrode (5), for a first period of first predetermined duration (D1),
applying another direct current, referred to as second direct current, of predetermined value, referred to as second value, and predetermined polarity, referred to as second polarity, opposed to the first polarity, between the first electrode (2) and the third electrode (5), for a predetermined duration (D2), referred to as second duration (D2);
when the voltage (V) between the second electrode (4) and the third electrode (5) has been measured during said first predetermined duration (D1),
measuring the voltage (V) between the second electrode (4) and the third electrode (5) during said second predetermined duration (D2), and then storing these voltage values;
when comparing the variations in the voltage (V) between the second electrode (4) and the third electrode (5) during the first predetermined duration (D1) with predetermined data defining at least whether or not a mixture has passivating properties, and determining at least whether or not the mixture (11) has such passivating properties, also comparing the variations in the voltage (V) between the second electrode (4) and the third electrode (5) during said second predetermined duration (D2).

4. The method according to claim 3, characterized in that the step of selecting the first electrode (2) and the third electrode (5) and applying a first direct current and then a second direct current between these two electrodes involves the use of a first direct current and a second direct current with:
a first predetermined polarity and a second predetermined polarity that are opposite, and
a first duration (D1) and a second duration (D2) that are equal.

5. The method according to claim 4, characterized in that the steps of comparing the variations in the voltage (V) between the second electrode (4) and the third electrode (5) during the first predetermined duration (D1) and the second predetermined duration (D2), with predetermined data defining at least whether or not a mixture (11) has passivating properties, and determining at least whether or not the mixture (11) has such passivating properties,
a) checking whether the difference, referred to as first voltage difference (V1), between the maximum voltage value of the first predetermined duration (D1) and the voltage value as a predetermined instant (T1), referred to as first predetermined instant (T1), of the first predetermined duration (D1), exceeds a first predetermined voltage value, or not, and/or
b) checking whether the difference, referred to as second voltage difference (V2), between the maximum voltage value of the first predetermined duration (D1) and the voltage value at a predetermined instant (T2), referred to as second predetermined instant, of the second predetermined duration (D2), is within a first predetermined range, or not, and/or
c) checking whether the difference, referred to as third voltage difference (V3), between the voltage value at a predetermined instant (T3), referred to as third predetermined instant (T3), of the first predetermined duration (D1) and the voltage (V) at a predetermined instant (T4), referred to as fourth predetermined instant (T4), of the second predetermined duration (D2) is within a second predetermined range, or not.

6. The method according to claim 5, characterized in that for the step of comparing the variations in the voltage (V) between the second electrode (4) and the third electrode (5) with predetermined data defining at least whether or not a mixture has passivating properties, when:
the first voltage difference (V1) is a maximum of fifty millivolts (50 mV) (first predetermined voltage value),
the second voltage difference (V2) is one point eight volts to two point three volts (1.8 V to 2.3 V) (first predetermined range), and
the third voltage difference V3 is one point eight volts to two point three volts (1.8 V to 2.3 V) (second predetermined range), the conclusion is that the mixture (11) has passivating properties, at least in the vicinity of the third electrode (5).

7. The method according to claim 5, characterized in that in the step of comparing the variations in the voltage (V0 between the second electrode (4) and the third electrode (5) with predetermined data defining at least whether or not a mixture (11) has passivating properties, when the change is potential between the fourth second of at least one of the first (D1) and second (D2) predetermined duration, and the ninth second of at least one of the first (D1) and second (D2) predetermined duration is more than six millivolts (6 mV), the conclusion is that the third electrode (5) is in contact with a mixture (11) made up of hardening cement and water, instead of only bleed water, that is to say liquid emerging from a mixture (11) of water and cement.

8. The method according to claim 3, characterized in that for the step of selecting the first electrode (2) and the third electrode (5) and applying between these two electrodes a first direct current of first predetermined polarity, for a first predetermined duration (D1), and then a second direct current of second polarity opposed to the first polarity, for a second predetermined duration (D2):

the first direct current is such that a density of current of two point five milliampere per square centimeter (2.5 mA/cm$^2$) emerges from the third electrode (5), and the second direct current is such that a density of current of two point five milliampere per square centimeter (2.5 mA/cm$^2$) emerges from the first electrode (2).

9. The method according to claim 1, characterized in that the value of at least one of the first predetermined duration (D10) and the second predetermined duration (D2) is between one second and thirty seconds.

10. The method according to claim 1, characterized in that at least one of the first predetermined duration (D1) and the second predetermined duration (D2) is of ten seconds (10 s).

11. The method according to claim 1, characterized in that at least one of these two conditions is satisfied:

at least one of the first predetermined instant (T1) and the fourth predetermined instant (T4) is between ten percent and one hundred percent of the value of the first predetermined duration (D1), and at least one of the second predetermined instant (T2) and the third predetermined instant (T3) is between ten percent and one hundred percent of the value of the second predetermined duration (D2).

12. The method according to claim 1, characterized in that at least one of these two conditions is satisfied:

at least one of the first predetermined instant (T1) and the fourth predetermined instant (T4) is equal to ninety percent of the value of the first predetermined duration (D1), and at least one of the second predetermined instant (T2) and the third predetermined instant (T3) is equal to ninety percent of the value of the second predetermined duration (D2).

13. The method according to claim 1, characterized in that the step consisting of taking three elements, each made up of an electrically conductive material, these elements being said first electrode (20, second electrode (4) and third electrode (5), each of these three electrodes having at least one face (20, 40, 50), comprises the operation of selecting three elements each made up of steel.

14. The method according to claim 1, characterized in that the change in potential in the solid mixture is used to determine the alkalinity of the mixture (11) at any later point in time.

15. The method according to claim 1, characterized in that measuring the potential polarization resistance of the second electrode (4) is used for monitoring of the corrosion behavior over time.

16. A sensor for determining the passivating properties of a mixture (11) containing at least two components, which are cement and water, according to the method of claim 1, this sensor being characterized in that it has:

three elements, each made up of an electrically conductive material, these elements, having at least one predetermined face, referred to as first face (20), second face (40) and third face (50), intended to come in contact with the mixture (11), being separately connected to an electric conductor intended to permit connection to a separate device, in such a manner that each of these three elements is capable of having the function of a first electrode (2), a second electrode (4) and a third electrode (5), and a support (3) for supporting at least one of the three elements in such a manner that they are electrically insulated reciprocally, and the mixture (11) is able to come in contact with all the faces, said first face (20), second face (40) and third face (50).

* * * * *